(12) United States Patent
O'Connell et al.

(10) Patent No.: US 11,298,154 B2
(45) Date of Patent: Apr. 12, 2022

(54) GUIDE EXTENSION CATHETER ASSEMBLIES, SYSTEMS AND METHODS OF USE

(71) Applicant: Medtronic Vascular, Inc., Santa Rosa, CA (US)

(72) Inventors: Barry O'Connell, Galway (IE); Sean Ward, Galway (IE); John K. Tuohy, Clare (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 238 days.

(21) Appl. No.: 16/539,280

(22) Filed: Aug. 13, 2019

(65) Prior Publication Data

US 2020/0060722 A1 Feb. 27, 2020

Related U.S. Application Data

(60) Provisional application No. 62/720,670, filed on Aug. 21, 2018.

(51) Int. Cl.
*A61B 17/00* (2006.01)
*A61B 17/34* (2006.01)
(Continued)

(52) U.S. Cl.
CPC .... *A61B 17/3423* (2013.01); *A61B 17/00234* (2013.01); *A61B 2017/00292* (2013.01);
(Continued)

(58) Field of Classification Search
CPC ...... A61M 2025/0681; A61M 25/0662; A61M 25/104; A61M 25/09041; A61M 25/0068; A61M 2025/0687; A61M 2025/0175; A61M 25/0169; A61M 25/0905; A61M 2025/0004; A61M 25/0102;
(Continued)

(56) References Cited

U.S. PATENT DOCUMENTS 8,048,032 B2 11/2011 Root et al.
8,996,095 B2 3/2015 Anderson et al.
(Continued)

OTHER PUBLICATIONS

PCT/US2019-046343, The International Search Report and Written Opinion, dated Nov. 27, 2019, 16pgs.

*Primary Examiner* — Dianne Dornbusch
(74) *Attorney, Agent, or Firm* — Dicke, Billig & Czaja, PLLC

(57) ABSTRACT

A guide extension catheter assembly including a guide extension catheter and a support device. The guide extension catheter includes a shaft and a tubular member. The support device includes a push member and a shuttle member. The guide extension catheter assembly is configured to selectively provide a delivery state in which at least a portion of the shuttle member is disposed within the lumen, a leading end of the shuttle member is distal a distal end of the tubular member, and the shuttle member is directly, physically connected to the tubular member. In the delivery state, a longitudinal distal force applied to the push member is transferred to the tubular member as a longitudinal distal force via the shuttle member. The guide extension catheter assemblies of the present disclosure can promote a two stage guide extension catheter deployment.

20 Claims, 14 Drawing Sheets

(51) Int. Cl.
*A61M 25/09* (2006.01)
*A61M 25/00* (2006.01)
*A61M 25/06* (2006.01)

(52) U.S. Cl.
CPC .... *A61B 2017/3425* (2013.01); *A61M 25/007* (2013.01); *A61M 25/09* (2013.01); *A61M 2025/0687* (2013.01)

(58) Field of Classification Search
CPC .......... A61M 25/0069; A61M 25/0105; A61M 25/0009; A61B 2017/3425; A61B 17/00234; A61B 2017/00292
See application file for complete search history.

(56) References Cited

U.S. PATENT DOCUMENTS

| | | | |
|---|---|---|---|
| 2005/0027236 A1* | 2/2005 | Douk | A61M 1/84 604/40 |
| 2009/0264865 A1 | 10/2009 | Kawai | |
| 2010/0030186 A1* | 2/2010 | Stivland | A61M 25/09 604/510 |
| 2013/0116701 A1 | 5/2013 | Wang et al. | |
| 2013/0237962 A1 | 9/2013 | Kawai | |
| 2014/0012281 A1* | 1/2014 | Wang | A61M 25/0023 606/108 |
| 2014/0018773 A1* | 1/2014 | Wang | A61M 25/0069 604/510 |
| 2014/0025043 A1* | 1/2014 | Wang | A61M 25/0102 604/528 |
| 2014/0052097 A1* | 2/2014 | Petersen | A61M 25/01 604/506 |
| 2015/0173782 A1* | 6/2015 | Garrison | A61B 17/320758 606/127 |
| 2016/0346502 A1* | 12/2016 | Fuller | A61M 25/0069 |
| 2017/0080178 A1 | 3/2017 | O'Connell et al. | |
| 2017/0252043 A1 | 9/2017 | Fuller et al. | |
| 2017/0296783 A1 | 10/2017 | Connolly et al. | |
| 2017/0354800 A1* | 12/2017 | O'Donovan | A61M 25/0662 |
| 2018/0064453 A1* | 3/2018 | Garrison | A61B 17/221 |
| 2018/0104445 A1* | 4/2018 | Fuller | A61M 25/10 |
| 2018/0126121 A1* | 5/2018 | Mauch | A61F 2/95 |
| 2018/0161547 A1 | 6/2018 | Brenizer et al. | |
| 2018/0207339 A1 | 7/2018 | Chou et al. | |
| 2019/0255297 A1 | 8/2019 | Fischell et al. | |
| 2019/0255299 A1* | 8/2019 | Fischell | A61F 2/958 |

* cited by examiner

GUIDE EXTENSION CATHETER ASSEMBLIES, SYSTEMS AND METHODS OF USE

CROSS-REFERENCE TO RELATED APPLICATIONS

This Non-Provisional patent application claims the benefit of the filing date of U.S. Provisional Application Ser. No. 62/720,670 filed Aug. 21, 2018, the entire teachings of which are incorporated herein by reference.

FIELD

Aspects of the present disclosure relate to guide catheter systems for accessing intravascular target sites, guide extension catheters useful with such systems, and methods of use thereof.

BACKGROUND

Arteries of the heart, and more specifically coronary arteries, may sometimes be occluded or narrowed by atherosclerotic plaques or other lesions. These afflictions are generally referred to as coronary heart disease or stenosis, and result in inadequate blood flow to distal arteries and tissue. Heart bypass surgery may be a viable surgical procedure for certain patients suffering from coronary heart disease. However, traditional open heart surgery may inflict significant patient trauma and discomfort, and may require extensive recuperation times. Further, life threatening complications may occur due to the invasive nature of the surgery and the necessity for stoppage of the heart during such a surgery.

To address these concerns, efforts have been made to perform interventional cardiology procedures using minimally invasive techniques. In an example, percutaneous transcatheter (or transluminal) delivery and implantation of interventional coronary device are employed to overcome the problems presented by traditional open heart surgery. In such a procedure, a guide catheter is first interested through an incision into a femoral (transfemoral) or radial (transradial) artery of a patient. For example, the Seldinger technique may be utilized in either method for percutaneously introducing the guide catheter. In such methods, the guide catheter is advanced through the aorta and inserted into the opening of an ostium of a coronary artery. A guidewire, or other interventional coronary device, such as a catheter-mounted stent and/or balloon catheter, may be introduced through the guide catheter and maneuvered/advanced through the vasculature and the stenosis of the diseased coronary artery. However, when attempting to pass through a difficult stenosis, or when conducting a radial intervention using a small diameter guide catheter, the guide catheter may not have adequate back support, and continued application of force to advance the interventional coronary device through the stenosis may cause the distal end of the guide catheter to dislodge from the opening of the ostium of the coronary artery, resulting in potential damage to the surrounding tissue.

In order to prevent the guide catheter from dislodging, interventional cardiologists sometimes would deep seat the guide catheter into the coronary artery. The term "deep seat" or "deep seating" means that the guide catheter would be pushed farther downstream into the coronary artery. However, deep seating the guide catheter may risk the guide catheter damaging the coronary artery wall (e.g., dissection or rupture), occluding the coronary artery, or interfering with blood flow to the coronary artery.

One attempt to provide additional support to a guide catheter that has gained acceptance is the use of a guide extension catheter. The guide extension catheter is deployed within a lumen of the guide catheter and extends distally from the distal end of the guide catheter into the coronary artery. Their smaller size, as compared to the guide catheter, allows the guide extension catheter to be seated more deeply in the coronary artery with less potential damage. The guide extension catheter provides additional support to the guide catheter to aid in delivery of interventional coronary devices. In cases with a difficult stenosis or radial interventions, the use of the guide extension catheter may reduce the risk of the guide catheter dislodging from the opening of the ostium of the coronary artery during treatment.

SUMMARY

Some aspects of the present disclosure related to a guide extension catheter assembly including a guide extension catheter and a support device. The guide extension catheter includes a shaft and a tubular member. The tubular member defines a proximal end opposite a distal end, and a lumen open to the proximal and distal ends. The shaft is coupled to the tubular member at the proximal end and extends proximally from the proximal end. The support device includes a push member and a shuttle member. The shuttle member defines a leading end opposite a trailing end. The push member is coupled to the shuttle member at the trailing end and extends proximally from the trailing end. The guide extension catheter assembly is configured to selectively provide a delivery state in which at least a portion of the shuttle member is disposed within the lumen, the leading end is distal the distal end, and the shuttle member is directly, physically connected to the tubular member. In the delivery state, a longitudinal distal force applied to the push member is transferred to the tubular member as a longitudinal distal force via the shuttle member. The guide extension catheter assemblies of the present disclosure can promote a two stage guide extension catheter deployment; the shuttle member promotes delivery of the tubular member and can then be removed with the tubular member then facilitating guide extension catheter procedures. In some embodiments, the guide extension catheter assembly includes complementary connection features that selectively provide direct, physical connection between the tubular member and the shuttle member. In some embodiments, the tubular member defines a plurality of perfusion holes and/or other features conducive to guide extension catheter procedures.

Other aspects of the present disclosure are directed toward a coronary treatment system including a guide catheter, a guide extension catheter assembly, and an interventional coronary device. The guide extension catheter assembly includes a guide extension catheter and a support device. The guide extension catheter includes a shaft and a tubular member. The tubular member defines a proximal end opposite a distal end, and a lumen open to the proximal and distal ends. The shaft is coupled to the tubular member at the proximal end and extends proximally from the proximal end. The support device includes a push member and a shuttle member. The shuttle member defines a leading end opposite a trailing end. The push member is coupled to the shuttle member at the trailing end and extends proximally from the trailing end. The guide extension catheter assembly is configured to selectively provide a delivery state in which at least a portion of the shuttle member is disposed within the lumen, the leading end is distal the distal end, and the shuttle member is directly, physically connected to the tubular member. In the delivery state, a longitudinal distal force applied to the push member is transferred to the tubular member as a longitudinal distal force via the shuttle member. In some embodiments, the guide catheter defines a lumen through sized to slidably receive the tubular member and the shuttle member in the delivery state, as well as a working end of the interventional coronary device. In other embodiments, the system further includes a guidewire in addition to the interventional coronary device.

Yet other aspects of the present disclosure are directed toward methods of percutaneously accessing an intravascular target region. The methods include positioning a distal side of a guide catheter adjacent to an ostium of a target vessel. A guide extension catheter assembly is arranged to a delivery state. The guide extension catheter assembly includes a guide extension catheter and a support device. The guide extension catheter includes a shaft and a tubular member. The tubular member defines a proximal end opposite a distal end, and a lumen open to the proximal and distal ends. The shaft is coupled to the tubular member at the proximal end and extends proximally from the proximal end. The support device includes a push member and a shuttle member. The shuttle member defines a leading end opposite a trailing end. The push member is coupled to the shuttle member at the trailing end and extends proximally from the trailing end. The delivery state includes at least a portion of the shuttle member disposed within the lumen, the leading end distal the distal end, and the shuttle member directly, physically connected to the tubular member. In the delivery state, a longitudinal distal force applied to the push member is transferred to the tubular member as a longitudinal distal force via the shuttle member. The guide extension catheter assembly is advanced in the delivery state through the guide catheter such that at least a region of the tubular member projects distally beyond the distal side of the guide catheter. The guide extension catheter assembly is transitioned from the delivery state, including removing the support device from the guide extension catheter. An interventional coronary device (e.g., a catheter-based device carrying a stent) is then advanced through the guide catheter and the tubular member. In some embodiments, the methods further include used of a guidewire to direct one or more of the guide catheter and the guide extension catheter assembly.

DETAILED DESCRIPTION

Specific embodiments of the present disclosure are now described with reference to the figures, wherein like reference numbers indicate identical or functionally similar elements. The terms "distal" and "proximal" are used in the present disclosure with respect to a position or direction relative to the treating clinician. "Distal" or "distally" refer to positions distant from or in a direction away from the clinician. "Proximal" and "proximally" refer to positions near or in a direction toward the clinician.

Figure 1A:
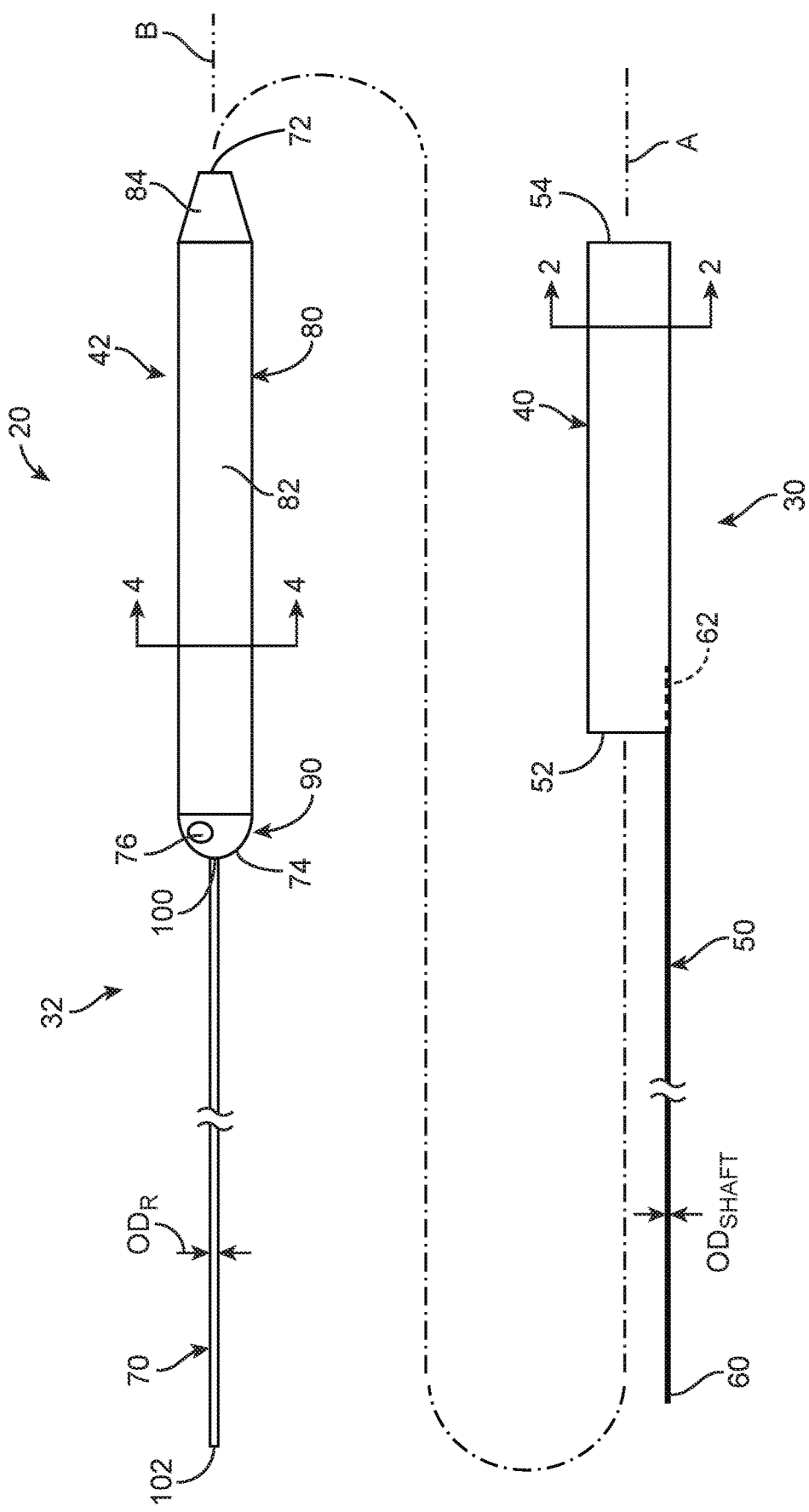
FIG. 1A is an exploded side view of a guide extension catheter assembly in accordance with principles of the present disclosure.
Figure 1B:
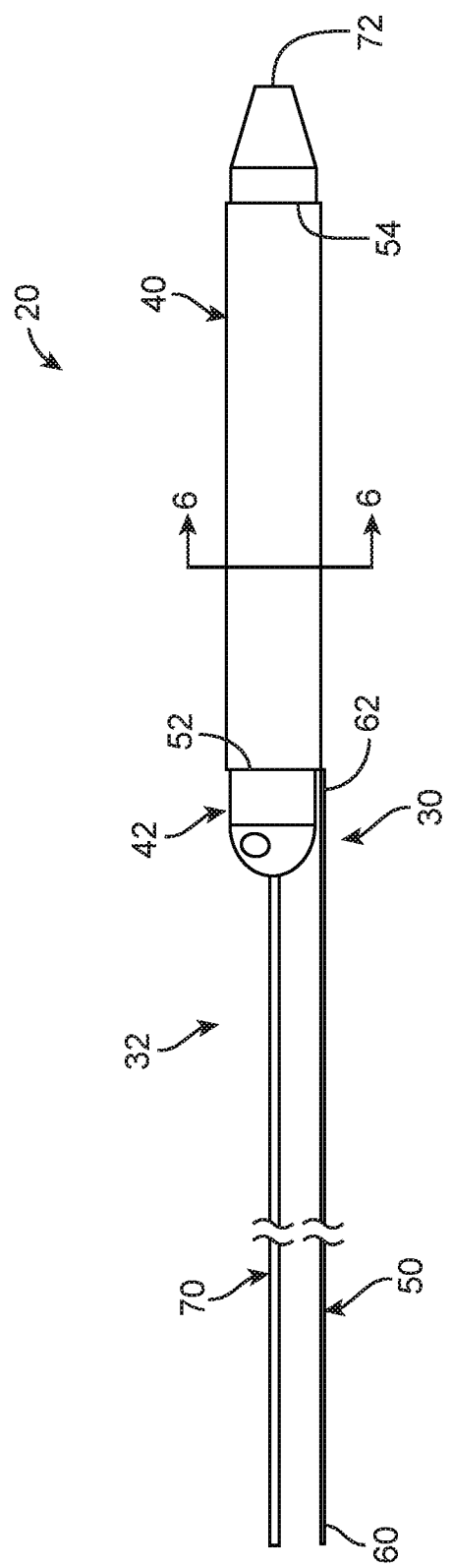
FIG. 1B is a side view of the guide extension catheter assembly of FIG. 1A in a delivery state.

One embodiment of a guide extension catheter assembly 20 in accordance with principles of the present disclosure and useful with systems and methods of the present disclosure is shown in FIGS. 1A and 1B, and includes a guide extension catheter 30 and a support device 32. Details on the various components are provided below. In general terms, the guide extension catheter 30 includes a tubular member 40, and the support device 32 includes a shuttle member 42. In a delivery state of the guide extension catheter assembly 20 reflected by FIG. 1B, the shuttle member 42 is disposed within the tubular member 40, and can promote delivery or advancement of the guide extension catheter assembly 20 through a tortuous path (e.g., vasculature). Once a desired location has been attained, the shuttle member 42 can be removed from the tubular member 40, and the guide extension catheter 30 is available for other procedural steps. For example, the tubular member 40 can serve as an extension of a conventional guide catheter. With some guide extension catheter assemblies 20 of the present disclosure, attributes conducive to intravascular traversal can be incorporated into a design of the support device 32 (e.g., hoop strength, longitudinal push strength, etc.), whereas attributes conducive to guidance and delivery of an interventional coronary device (not shown) can be incorporated into a design of the guide extension catheter 30. In some embodiments, complementary connection features are provided that provide direct, physical connection between the tubular member 40 and the shuttle member 42 in the delivery state as described below.

The guide extension catheter 30 can assume various forms, and includes the tubular member 40 and a shaft 50. As described below, the shaft 50 is coupled to, and extends proximally from, the tubular member 40. As a point of reference, in some non-limiting embodiments the guide extension catheter 30 can have a length on the order of 150 centimeters (cm), with the tubular member 40 being approximately 20-40 cm in length. However, this is not meant to limit the present disclosure, and the guide extension catheter 30 and/or the tubular member 40 thereof may be longer or shorter.

Figure 2:
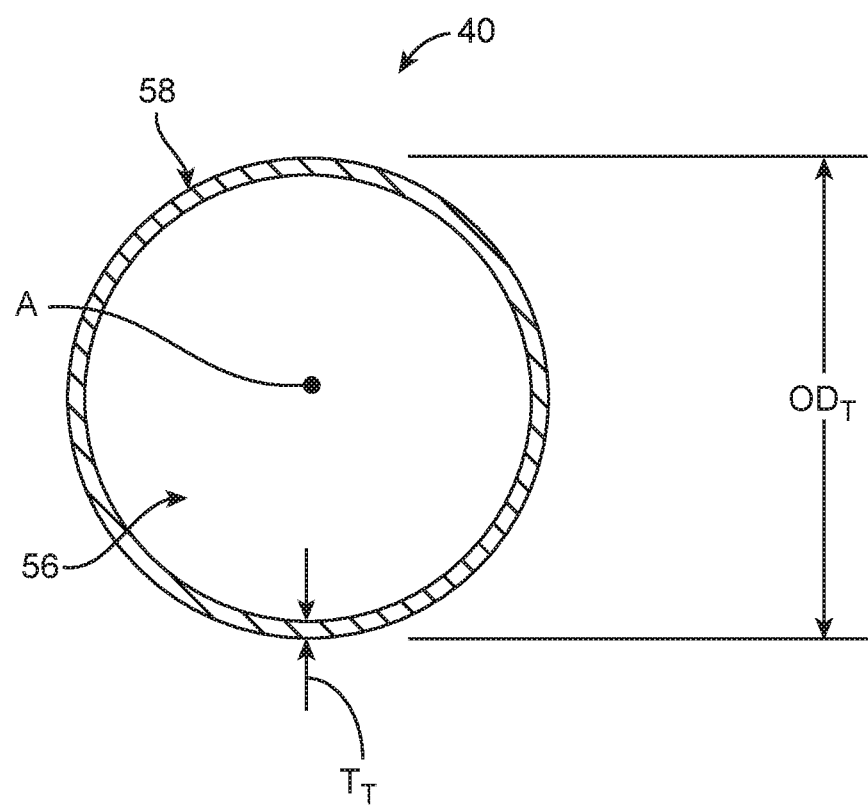
FIG. 2 is an enlarged cross-sectional view of a tubular member component of a guide extension catheter of the guide extension catheter assembly of FIG. 1A, taken along the line 2-2.

With reference between FIGS. 1A and 2, the tubular member 40 defines a proximal end 52 opposite a distal end 54, and a lumen 56 open at the proximal and distal ends 52, 54. The lumen 56 is sized to receive a device, such as an interventional coronary device (not shown) as described below, for guiding the device along a longitudinal axis A of the tubular member 40. Further, an outer diameter ODT of the tubular member 40 can be selected in accordance with a desired end use as described below (e.g., the outer diameter ODT can be selected such that the tubular member 40 can be slidably received within a guide catheter being employed with a particular end use procedure).

The tubular member 40 can be formed of various materials, non-limiting examples of which include polymers and braided polymers. In the representation of FIG. 2, a structure of the tubular member 40 is illustrated as being defined by a wall 58. The wall 58 can have a homogenous or monolithic construction as shown. In other embodiments, the wall 58 can be collectively formed by two or more continuous or discontinuous layers (e.g., an inner liner and outer jacket sandwiching one or more wires or other reinforcement bodies). Regardless, the wall 58 has a wall thickness TT and provides the tubular member 40 with physical attributes including hoop strength and longitudinal column rigidity or stiffness (i.e., extent to which the tubular member 40 resists deformation when subjected to a force along the longitudinal axis A).

Figure 3:
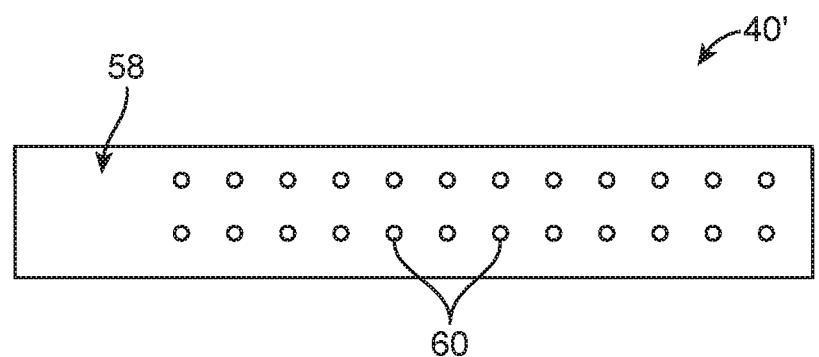
FIG. 3 is a simplified side view of an alternative tubular member useful with the guide extension catheter assemblies of the present disclosure.

In some embodiments, the tubular member 40 can be designed to incorporate attributes conducive to use of the tubular member 40 as an extension of a conventional guide catheter; in related embodiments, a design of the tubular member 40 need not directly account for or consider deliverability through a tortuous intravascular path (e.g., the tubular member 40 does not need to have or exhibit a hoop strength and/or longitudinal column rigidity normally considered necessary for intravascular delivery) due to provision of the support device 42 as described below. Thus, in some embodiments, the wall thickness TT can be less than the wall thickness conventionally employed with guide extension catheters. Along these same lines, FIG. 3 illustrates another tubular member 40' useful with the assemblies, systems and methods of the present disclosure. The tubular member 40' is akin to the tubular member 40 (FIG. 1A) described above, and includes the wall 58. In addition, a plurality of perfusion holes 60 are defined by or formed in the wall 58. The perfusion holes 60 can have wide variety of shapes and sizes, and can be formed in a number of different patterns. In general terms, the perfusion holes 60 are open to the lumen 56 (FIG. 2) and are configured to aid in continuous perfusion during use of the tubular member 40' as an extension of a conventional guide catheter. Although presence of the perfusion holes 60 might otherwise negatively affect deliverability of the tubular member 40' as a stand-alone device, the support device 32 (FIG. 1A) serves to facilitate delivery of the tubular member 40'. Other features can be incorporated into the tubular member 40' that enhance performance as an extension of a conventional guide catheter.

Returning to FIGS. 1A and 1B, the shaft 50, also referred to as a pushwire or push member, defines a proximal side 60 opposite a distal side 62. The distal side 62 is coupled to the tubular member 40 in a region of the proximal end 52, and the shaft 50 is arranged to extend proximally from the tubular member 40 to the proximal side 60. The shaft 50 may be formed of materials such as, but not limited to, stainless steel, nickel-titanium alloys (e.g., NITINOL), high performance alloys that are cobalt, chromium, molybdenum and/or nickel based (e.g., MP35N, L605, ELGILOY), or other materials suitable for the purposes described herein.

In some embodiments, the shaft 50 can be a solid body (e.g., a solid wire). In other embodiments, an internal passage can be defined along a portion or an entirety of the shaft 50. In some embodiments, the shaft 50 can have a uniform cross-sectional shape (e.g., circular, square, etc.) from the proximal side 60 to the distal side 62. In other embodiments, one or more variations in cross-sectional shape can be incorporated into the shaft 50 along a length thereof (e.g., the shaft 50 can have a varying thickness, the shaft 50 can have a more flattened shape proximate the tubular member 40, etc.). Regardless, a maximum outer dimension ODSHAFT of the shaft 50 is less than the outer diameter ODT (FIG. 2) of the tubular member 40.

Coupling of the shaft 50 with the tubular member 40 can assume various forms appropriate for providing a robust connection. For example, in some non-limiting embodiments, a segment of the shaft 50, including the distal side 62, can be embedded into a thickness of the tubular member 40. Alternatively, the shaft 50 can be secured (e.g., bonded) to an exterior or interior surface of the tubular member 40. In yet other embodiments, a connecting member (not shown) can be provided that secures the shaft 50 relative to the tubular member 40. For example, the shaft 50 can be attached to a collar that in turn is secured over an exterior of the tubular member 40.

With specific reference to FIG. 1A, the support device 32 can assume various forms, and includes the shuttle member 42 and a push member 70. As described below, the push member 70 is coupled to, and extends proximally from, the shuttle member 42. As a point of reference, in some non-limiting embodiments the support device 32 can have a length on the order of 150 cm, with the shuttle member 42 being approximately 20-40 cm in length (and optionally slightly longer than the tubular member 40. However, this is not meant to limit the present disclosure, and the support device 32 and/or the shuttle member 42 thereof may be longer or shorter.

Figure 4:
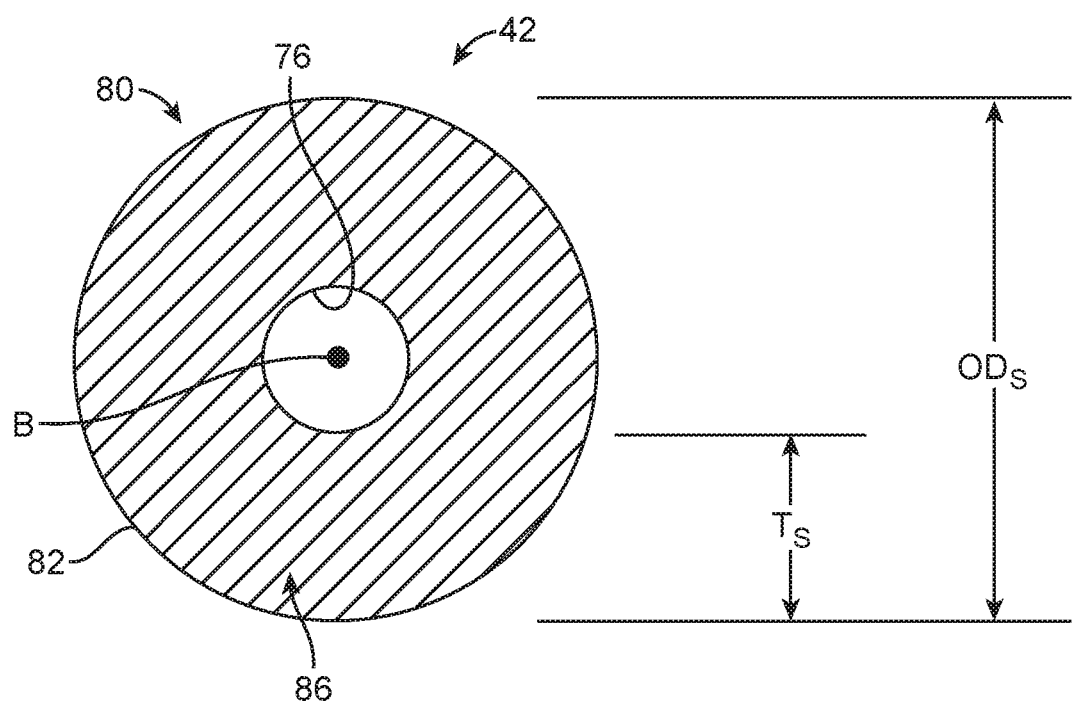
FIG. 4 is an enlarged cross-sectional view of a shuttle member component of a support device of the guide extension catheter assembly of FIG. 1A, taken along the line 4-4.

With reference between FIGS. 1A and 4, the shuttle member 42 defines a leading end 72 opposite a trailing end 74, and a passageway 76 (referenced generally in FIG. 1A). The passageway 76 is sized to receive a device, such as guidewire (not shown) as described below, and can be open to an exterior of the shuttle member 42 at the leading end 72 and in a region of the trailing end 74 for guiding the device along a longitudinal axis B of the shuttle member 42.

The shuttle member 42 can be a continuous, homogenous body in some embodiments. In other embodiments, the shuttle member 42 can include two or more sections that are separately formed and subsequently assembled. Regardless, an interface region 80 of the shuttle member 42 includes, and extends proximally from, the leading end 72. The interface region 80 has a length (i.e., dimension in a direction parallel with the longitudinal axis B) that is not less than a length of the tubular member 40, and defines a maximum outer dimension (e.g., outer diameter) ODs in a direction transverse to the longitudinal axis B. The maximum outer dimension ODs corresponds with (e.g., is slightly less than) a size or diameter of the tubular member lumen 56 (FIG. 2) such that the interface region 80 is configured to be readily received within the tubular member 40. In some embodiments, one or more portions of the shuttle member 42 proximal the interface region 80 can have an outer dimension greater than the maximum outer dimension ODs as described below. With these and similar constructions, however, the maximum outer dimension ODs can be identified along the shuttle member 42 from the leading end 72 to a location not less than a length of the tubular member 40. In other embodiments, an entirety of the shuttle member 42 has a maximum outer dimension approximating (e.g., slightly less than) a size or diameter of the tubular member lumen 56.

In some embodiments, the interface region 80 includes or is defined by a support section 82 and an optional tip section 84. The support section 82 is configured to receive and support the tubular member 40. For example, the support section 82 has a length (i.e., dimension in a direction parallel with the longitudinal axis B) that is not less than a length of the tubular member 40, and has a substantially uniform (i.e., within 10 percent of a truly uniform construction) exterior shape and size in a direction of the length of the shuttle member 42. In some embodiments, the support section 82 can define a circular exterior shape in transverse cross-section as shown in FIG. 4, although other shapes are acceptable. Regardless, the support section 82 defines the maximum outer dimension (e.g., outer diameter) ODs.

The support section 82, optionally an entirety of the shuttle member 42, can be formed of various materials, non-limiting examples of which include polymers (e.g., thermoplastic elastomer such as a polyether block amide thermoplastic elastomer available from Arkema of Colombes, FR under the tradename PEBAX®) and braided polymers. In the representation of FIG. 4, a structure of the support section 82 is illustrated as being defined by a wall 86. The wall 86 can have a homogenous or monolithic construction as shown. In other embodiments, the wall 86 can be collectively formed by two or more continuous or discontinuous layers (e.g., an inner liner and outer jacket sandwiching one or more wires or other reinforcement bodies). Regardless, the wall 86 has a wall thickness Ts and provides the shuttle member 42 with physical attributes including hoop strength and longitudinal column rigidity or stiffness (i.e., extent to which the shuttle member 42 resists deformation when subjected to a force along the longitudinal axis B). In some embodiments, the shuttle member 42, and in particular at least the support section 82, incorporates one or more features or attributes that render the shuttle member 42 more conducive to intravascular delivery as compared to the tubular member 40. For example, in some embodiments, the wall thickness Ts of the shuttle member 42 (at least along the support section 82) is greater than the wall thickness TT (FIG. 2) of the tubular member 40, for example at least 50% greater. Alternatively or in addition, a hoop strength of the shuttle member 42 along at least the support section 82 can be greater than the hoop strength of the tubular member 40, for example at least 50% greater. Alternatively or in addition, a longitudinal column rigidity or stiffness (i.e., extent to which the shuttle member 42 resists deformation when subjected to a force along the longitudinal axis B) of the shuttle member 42 along at least the support section 82 can be greater than the longitudinal column rigidity or stiffness of the tubular member 40. While the support section 82 is generally illustrated as having a shape akin to the shape of the tubular member 40 (e.g., circular shape in transverse cross-section), other formats are also acceptable. For example, an outer or perimeter shape of the support section 82 in transverse cross-section can include one or more linear segments (e.g., square, hexagonal, etc.), can have an irregular shape, etc.

Where provided, the tip section 84 tapers in the proximal direction from the support section 82 to the leading end 72, such that the tip section 84 promotes atraumatic interface with tissue. The atraumatic attributes of the tip section 84 can be further enhanced by forming the tip section 84 from a material differing from that of the support section 82; for example, a material of the tip section 84 can be a softer and/or more compliant than a material of the support section 82. In other embodiments, the shuttle member 42 need not include a tapered tip (e.g., the leading end 72 has the maximum outer dimension ODs).

Regardless of whether the shuttle member 42 includes a tapered tip, in some non-limiting embodiments, the shuttle member 42 can optionally further include or define a trailing region 90 extending proximally from the interface region 80. The trailing region 90 may have an exterior size and/or shape differing from that of the interface region 80, and in particular differing from the support section 82 (e.g., a portion of the trailing region 90 can have an outer dimension or diameter greater than the maximum outer dimension ODs of the support section 82, can taper distally to the trailing end 74, etc.).

The push member 70, also referred to as a pushwire or a shaft, defines a leading side 100 opposite a trailing side 102. The leading side 100 is coupled to the shuttle member 42 in a region of the trailing end 74, and the push member 70 is arranged to extend proximally from the shuttle member 42 to the trailing side 102. The push member 70 may be formed of materials such as, but not limited to, stainless steel, nickel-titanium alloys (e.g., NITINOL), high performance alloys that are cobalt, chromium, molybdenum and/or nickel based (e.g., MP35N, L605, ELGILOY), or other materials suitable for the purposes described herein.

In some embodiments, the push member 70 can be a solid body (e.g., a solid wire). In other embodiments, an internal passage can be defined along a portion or an entirety of the push member 70. In some embodiments, the push member 70 can have a uniform cross-sectional shape (e.g., circular, square, etc.) from the leading side 100 to the trailing side 102. In other embodiments, one or more variations in cross-sectional shape can be incorporated into the push member 70 along a length thereof (e.g., the push member 70 can have a varying thickness, the push member 70 can have a more flattened shape proximate the shuttle member 42, etc.). Regardless, a maximum outer dimension ODR of the push member 70 is less than the maximum outer dimension ODs of the shuttle member 42.

Coupling of the push member 70 with the shuttle member 42 can assume various forms appropriate for providing a robust connection. For example, in some non-limiting embodiments, a segment of the push member 70, including the leading edge 100, can be embedded into the shuttle member 42. Alternatively, the push member 70 can be secured (e.g., bonded) to an exterior or interior surface of the shuttle member 42. In yet other embodiments, a connecting member (not shown) can be provided that secures the push member 70 relative to the shuttle member 42. For example, the push member 70 can be attached to a collar that in turn is secured over an exterior of the shuttle member 42 (with the collar optionally being considered as a part or component of the shuttle member 42 (e.g., the trailing region 90)).

Figure 5A:
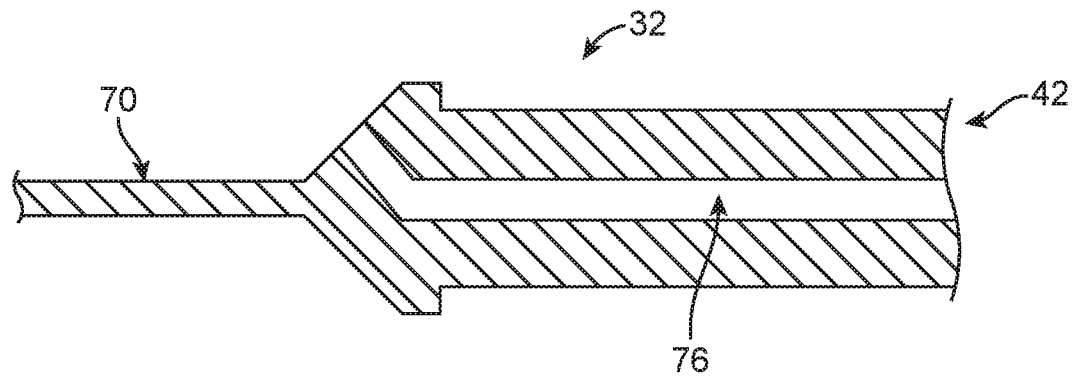
FIG. 5A is an enlarged, longitudinal cross-sectional view of a portion of the support device of FIG. 1A.
Figure 5B:
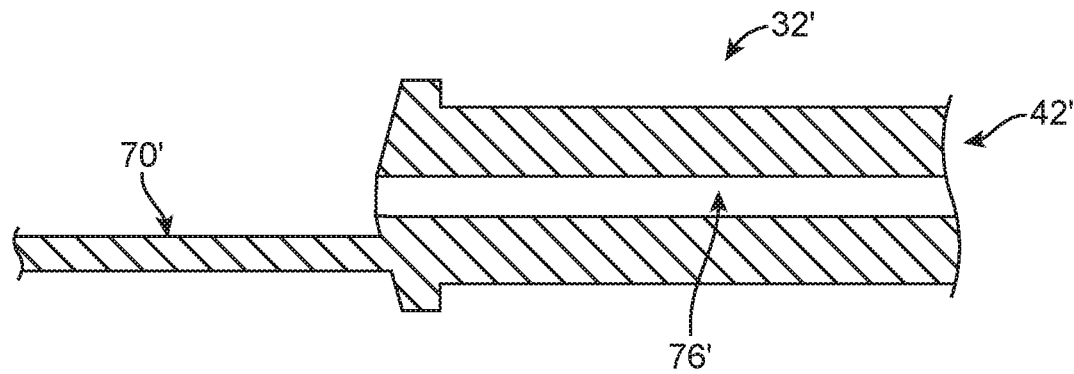
FIG. 5B is an enlarged, longitudinal cross-sectional view of a portion of another support device useful with the guide extension catheter assemblies of the present disclosure.

The push member 70 can be arranged relative to the shuttle member 42 in various manners. For example, FIG. 5A illustrates that in some non-limiting embodiments, the push member 70 can be approximately centered with or axially aligned with the shuttle member 42. FIG. 5A further reflects that with these and other embodiments, the passageway 76 can be non-linear across a length of the shuttle member 72. Another example support device 32' is shown in FIG. 5B and includes a shuttle member 42' and a push member 70' akin to the descriptions above. The shuttle member 42' defines a passageway 76' (e.g., for slidably receiving a guidewire (not shown)) that is linear across a length of the shuttle member 42'. The push member 70' extends proximally from the shuttle member 42' and is off-set from central or longitudinal axis of the shuttle member 42'. Other relationships between the shuttle member 42', the push member 70' and the passageway 76' are also envisioned.

Figure 6:
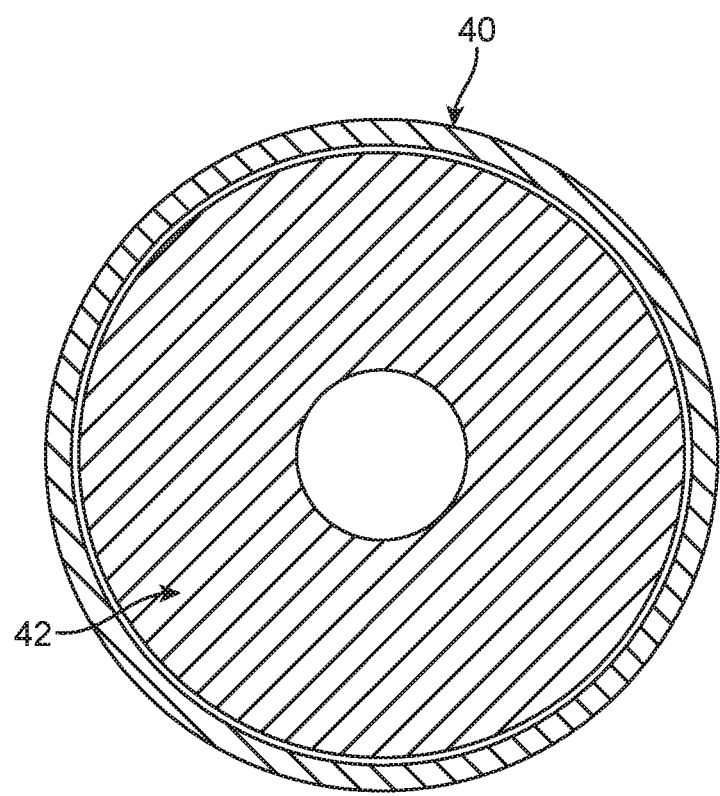
FIG. 6 is an enlarged cross-sectional view of the guide extension catheter assembly in the delivery state of FIG. 1B, taken along the line 6-6.

The guide extension catheter assembly 20 is transitioned to the delivery state of FIG. 1B by directing the leading end 72 of the shuttle member 42 into the lumen 56 (FIG. 2) of the tubular member 40 at the proximal end 52. The shuttle member 42 is then advanced distally relative to the tubular member 40 (and/or the tubular member 40 retracted proximally relative to the shuttle member 42), locating a length of the tubular member 40 over the shuttle member 42. Advancement and/or manipulation of the tubular member 40 and the shuttle member 42 relative to one another continues until the delivery state arrangement is achieved in which the leading end 72 of the shuttle member 42 is distal the distal end 54 of the tubular member 40, and the shuttle member 42 is directly, physically connected to the tubular member 40. In the delivery state, a longitudinal distal force applied to the push member 70 is transferred to the tubular member 40 as a longitudinal distal force via the shuttle member 42. As described in greater detail below, in some embodiments the tubular member 40 and the shuttle member 42 incorporate complimentary connection features that provide the direct, physical connection. Thus, in some embodiments and as reflected in FIG. 6, the tubular member 40 may be generally disposed over the shuttle member 42 but with sufficient clearance to allow for relatively easy withdrawal of the shuttle member 42 from the tubular member 40 when desired; with these and other embodiments, the complementary connection features provide the direct, physical connection between the tubular member 40 and the shuttle member 42 in a manner that provides an at least one directional "lock" between the tubular member 40 and the shuttle member 42 (e.g., in the delivery state, the tubular member 40 and the shuttle member 42 are locked relative to one another such that the shuttle member 42 cannot be further distally advanced relative to the tubular member 40 from the arrangement of FIG. 1B). Regardless, in the delivery state, the shuttle member 42 supports the tubular member 40, providing physical and/or mechanical properties that promote ease of intravascular deliverability (and which physical and/or mechanical properties are not fully provided by the tubular member 40 in and of itself).

Figure 7A:
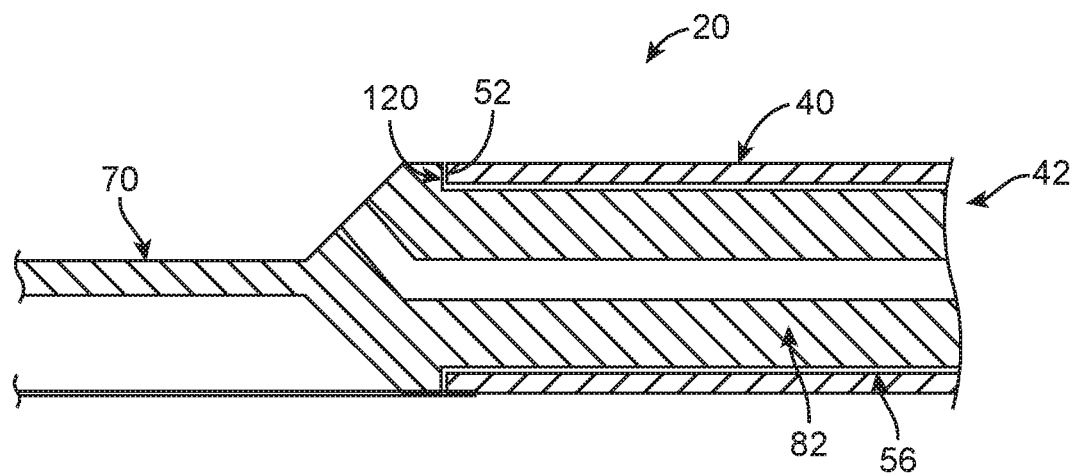
FIG. 7A is an enlarged cross-sectional view of a portion of the guide extension catheter assembly in the delivery state of FIG. 1B.

FIG. 7A depicts the tubular member 40 and the shuttle member 42 arranged in the delivery state, and further illustrates one example of complementary connection features in accordance with principles of the present disclosure. In particular, the shuttle member 42 includes or carries a shoulder 120, and the proximal end 52 of the tubular member 40 is sized and shaped to abut the shoulder 120 with distal insertion of the shuttle member 42 through the lumen 56. For example, an outer dimension or diameter of the support section 82 of the shuttle member 42 can approximate or be slightly less than a diameter of the lumen 56; the shoulder 120 extends radially outward from the support section 82 to an outer diameter greater than the diameter of lumen 56 and approximating an outer diameter of the tubular member 40. In the delivery state, the shoulder 120 directly, physically contacts the proximal end 52 to achieve or provide a direct, physical connection between the tubular member 40 and the shuttle member 42 in distal direction of the shuttle member 42 relative to the tubular member 40. That is to say, the direct, physical connection provided by the complementary connection features of the embodiment of FIG. 7A is such that a longitudinal distal force applied to the push member 70 is directly transferred onto the tubular member 40 as a distal longitudinal force via the abutting interface between the proximal end 52 of the tubular member 40 and the shoulder 120 of the shuttle member 42. Similarly, a longitudinal proximal force applied to the tubular member 40 (e.g., when encountering an anatomical structure during a delivery procedure) is directly transferred onto the shuttle member 42 via the abutting interface between the proximal end 52 of the tubular member 40 and the shoulder 120 of the shuttle member 42. In the presence of forces normally expected during a delivery procedure, once in the delivery state, the tubular member 40 will not move proximally relative to the shuttle member 42, and the shuttle member 42 will not move distally relative to the tubular member 40. The guide extension catheter assembly 20 can be transitioned from the delivery state to a released state by applying a pulling force in the proximal direction onto the shuttle member 42 while holding the tubular member 40 stationary. In the released state, the shuttle member 42 is free of direct, physical connection with the tubular member 40.

Figure 7B:
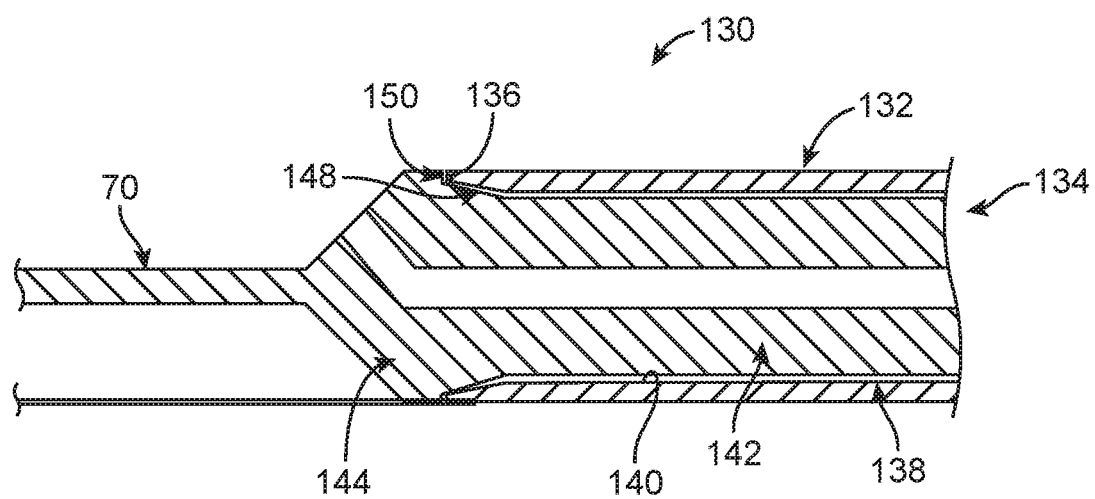
FIG. 7B is an enlarged cross-sectional view of a portion of another guide extension catheter assembly in a delivery state in accordance with principles of the present disclosure.

Portions of an alternative guide extension catheter assembly 130 are shown in FIG. 7B and illustrate another example of complementary connection features of the present disclosure. The guide extension catheter assembly is 130 is arranged in a delivery state and includes a tubular member 132 and a shuttle member 134. The tubular member 132 and the shuttle member 134 can have any of the forms described in the present disclosure. In this regard, the tubular member 132 defines a proximal end 136 and a lumen 138 bounded by an interior face 140. The shuttle member 134 includes a support section 142 and a trailing region 144. The support section 144 defines a support surface 146 sized and shaped to be slidably received within the lumen 138 as described above. The trailing region 144 defines a ramp surface 148 and a shoulder 150. The ramp surface 148 extends proximally from the support surface 146, expanding in diameter toward the shoulder 150. Thus, an outer dimension or diameter of the ramp surface 148 increases or expands in the proximal direction, from a diameter less than a diameter of the lumen 138 at the support surface 146 to a diameter greater than the diameter of the lumen 138 adjacent the shoulder 150. An outer dimension or diameter of the shoulder 150 can approximate or be greater than an outer diameter of the tubular member 132.

The complimentary connection features associated with the guide extension catheter assembly 130 include a configuration of a diameter of the lumen 138 at or proximate the proximal end 136, along with the ramp surface 148. With initial insertion of the shuttle member 134 into the lumen 138 via the proximal end 136, the shuttle member 134 is readily distally advanced relative to the tubular member 132 due to clearance between the interior face 140 and the support surface 146. As the ramp surface 148 enters the lumen 138, the ramp surface 148 is brought into direct, physical contact with the interior face 140 along those regions of the ramp surface 148 having a diameter greater than the diameter of the lumen 138. In the delivery state illustrated in FIG. 6B, a tapered fit or connection between the ramp surface 148 of the shuttle member 134 and the interior face 140 of the tubular member 132 has been obtained. In some embodiments, a material of the tubular member 132 compresses in response to forces exerted thereon by the ramp surface 148 with distal advancement of the shuttle member 134 relative to the tubular member 132. In other embodiments, a slight taper can be incorporated into a design of the tubular member 132 at the proximal end 136, with this taper angle approximating a taper angle of the ramp surface 148.

The direct, physical connection provided by the complementary connection features of the embodiment of FIG. 7B is such that a longitudinal distal force applied to the push member 70 (otherwise attached to the shuttle member 134) is directly transferred onto the tubular member 132 as a distal longitudinal force via the abutting interface between the interior face 140 of the tubular member 132 and the ramp surface 148 of the shuttle member 134. Similarly, a longitudinal proximal force applied to the tubular member 132 (e.g., when encountering an anatomical structure during a delivery procedure) is directly transferred onto the shuttle member 134 via the abutting interface between the interior face 140 of the tubular member 132 and the ramp surface 148 of the shuttle member 134. In the presence of forces normally expected during a delivery procedure, once in the delivery state, the tubular member 132 will not move proximally relative to the shuttle member 134, and the shuttle member 134 will not move distally relative to the tubular member 132. The guide extension catheter assembly 130 can be transitioned from the delivery state to a released state by applying a pulling force in the proximal direction onto the shuttle member 134 while holding the tubular member 132 stationary.

Figure 7C:
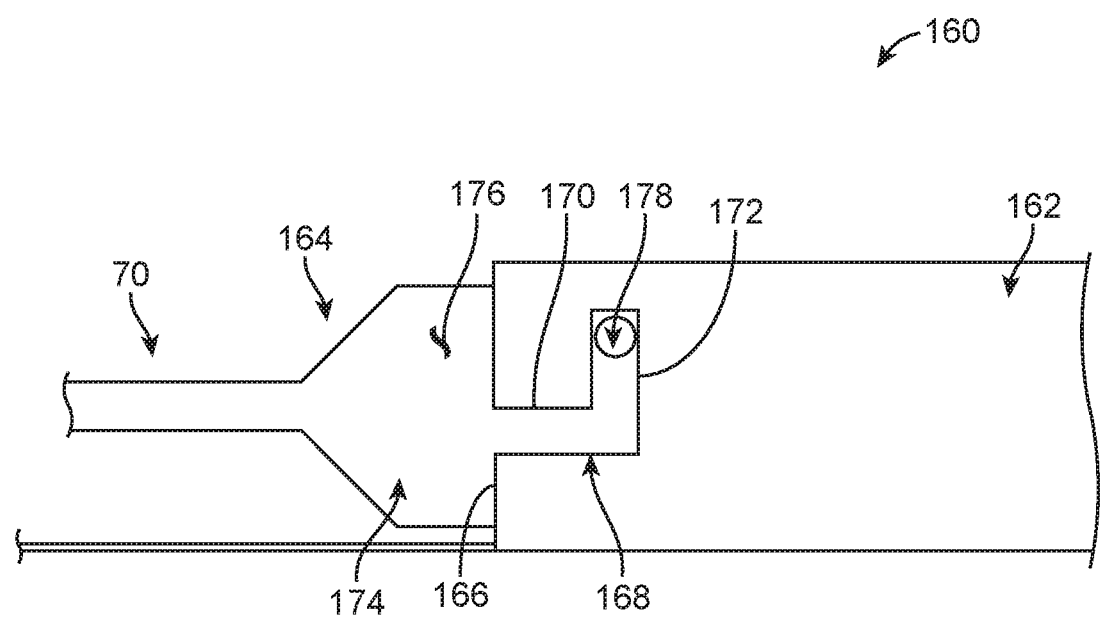
FIG. 7C is an enlarged side view of a portion of another guide extension catheter assembly in a delivery state in accordance with principles of the present disclosure.

Portions of another alternative guide extension catheter assembly 160 are shown in FIG. 7C and illustrate another example of complementary connection features of the present disclosure. The guide extension catheter assembly is 160 is arranged in a delivery state and includes a tubular member 162 and a shuttle member 164. The tubular member 162 can generally have any of the forms described in the present disclosure. In this regard, the tubular member 162 defines a proximal end 166 and a lumen (hidden). Further, a slot 168 is formed through a wall of the tubular member 162, extending from and open to the proximal end 166. The slot 168 can have a first segment 170 and a second segment 172. In some embodiments, the first segment 170 extends from the proximal end 166 in a generally longitudinal direction (e.g., parallel with a central longitudinal axis of the tubular member 162). The second segment 172 extends from the first segment 170 opposite the proximal end 166, defining a non-parallel angle relative to the first segment 170. For example, an angle defined by the first and second segments 170, 172 can be in the range of approximately 70-110 degrees, and in some embodiments, the second segment 172 extends in a circumferential fashion relative to a circumference of the tubular member 162.

The shuttle member 164 can generally have any of the forms described in the present disclosure. In this regard, the shuttle member 164 includes a support section 174 defining a support surface 176 and a post 178. The support surface 176 is sized and shaped to be slidably received within the lumen (not shown) of the tubular member 162 as described above. The post 178 projects radially outwardly from the support surface 176 and is sized and shaped to be slidably received within the slot 168.

The complimentary connection features associated with the guide extension catheter assembly 160 include a configuration of the slot 168 and the post 178. With initial insertion of the shuttle member 164 into the lumen (not shown) of the tubular member 162 via the proximal end 166, the shuttle member 164 is readily distally advanced relative to the tubular member 162 due to clearance between the support surface 176 and the tubular member 162. With continued distal advancement, as the post 178 approaches the proximal end 166, the shuttle member 164 is rotationally oriented such that the post 178 is longitudinally aligned with the slot 168 at the proximal end 166. With further distal advancement, then, the post 178 will enter the slot 168 and progress along the first segment 170. Upon reaching the transition from the first segment 170 to the second segment 172, the shuttle member 164 is rotated relative to the tubular member 162 such that the post 178 slides within the second segment 172 to the arrangement of FIG. 7C.

The direct, physical connection provided by the complementary connection features of the embodiment of FIG. 7C is such that a longitudinal distal force applied to the push member 70 (otherwise attached to the shuttle member 164) is directly transferred onto the tubular member 162 as a distal longitudinal force via the abutting interface between a structure of the tubular member 162 surrounding the slot 168 and the post 178 of the shuttle member 164. Similarly, a longitudinal proximal force applied to the tubular member 162 (e.g., when encountering an anatomical structure during a delivery procedure) is directly transferred onto the shuttle member 164 via the abutting interface between the tubular member 162 and the post 178 in a region of the slot 168. In the presence of forces normally expected during a delivery procedure, once in the delivery state, the tubular member 162 will not move relative to the shuttle member 164, and the shuttle member 164 will not move relative to the tubular member 162. The guide extension catheter assembly 160 can be transitioned from the delivery state to a released state by reversing the above steps, such as rotating the shuttle member 164 relative to the tubular member 162 to move the post 178 to the first segment 172, and then applying a pulling force in the proximal direction onto the shuttle member 164 while holding the tubular member 162 stationary.

The guide extension catheter assemblies of the present disclosure can be useful with a number of different procedures, such as procedures that entail percutaneously accessing an intravascular target region. With these and other procedures, the guide extension catheter assemblies of the present disclosure can be provided to a clinician as part of a coronary treatment system that further includes a guide catheter and an interventional coronary device. The guide catheter can have a conventional design. The interventional coronary device can be any device for treating, for example, an abnormal condition of a coronary artery, such as, but not limited to, a stenosis. Non-limiting examples of interventional coronary devices include guidewires, a catheter-based treatment device (e.g., a balloon catheter carrying an expandable stent, a catheter carrying a self-expanding stent, a fractional flow reserve (FFR) catheter), etc. In some embodiments, the coronary treatment systems of the present disclosure include at least one guidewire along with an additional or separate interventional coronary device that is not a guidewire.

Figure 8A:
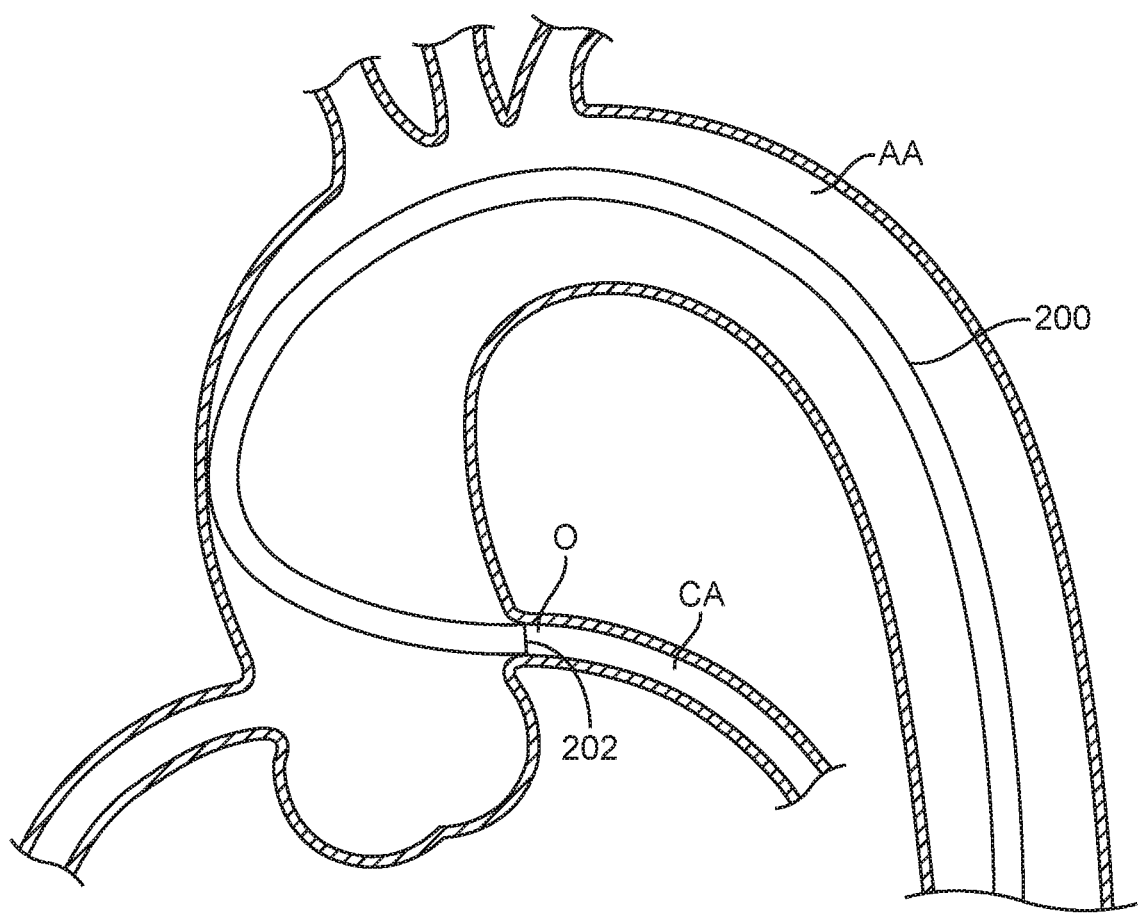
FIGS. 8A-8E illustrate methods of percutaneously accessing an intravascular target region in accordance with principles of the present disclosure, including methods of using a coronary treatment system including a guide extension catheter assembly.

With reference to FIG. 8A, some methods of the present disclosure can include delivering a treatment device to a desired treatment location, such as in a coronary artery CA that is accessed through the aorta AA. A guide catheter 200 can be utilized to access the aorta AA as shown. Generally, the guide catheter 200 includes a lumen sized to receive an auxiliary device or devices (e.g., a guide extension catheter assembly, an interventional coronary device, etc.). In some embodiments, a guidewire (not shown) can be deployed to assist in delivering the guide catheter 200 to the general arrangement of FIG. 8A. Regardless, the guide catheter 200 is arranged such that a distal side 202 thereof is at or adjacent an ostium O of the coronary artery CA.

Figure 8B:
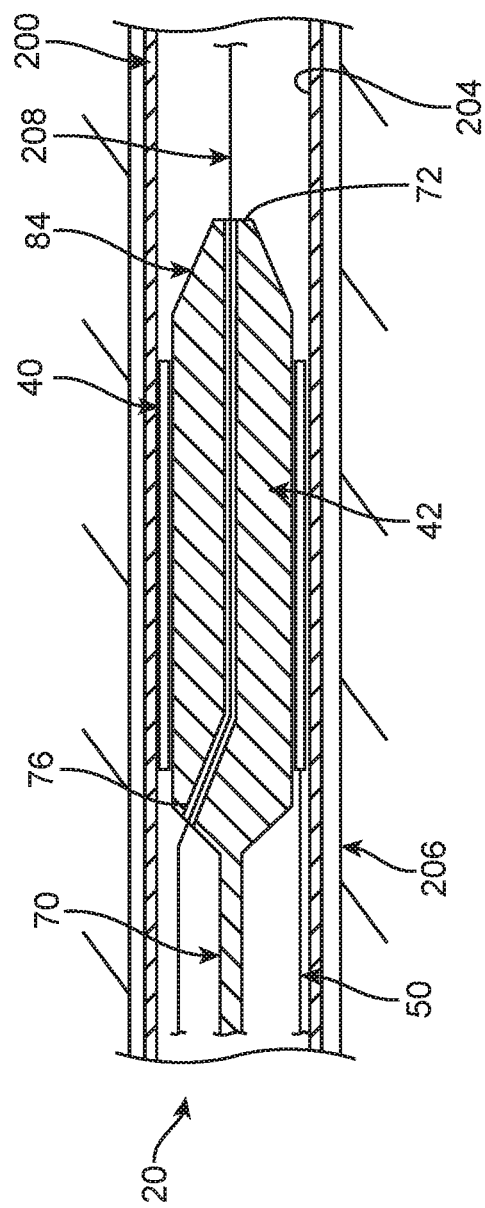

A guide extension catheter assembly of the present disclosure is arranged into the delivery state and advanced through the guide catheter 200. For example, FIG. 8B illustrates a portion of the guide extension catheter assembly 20 in the delivery state and being advanced within a lumen 204 of the guide catheter 200 that has otherwise been advanced through an intravascular passage 206 along with a guidewire 208. The tubular member 40 is disposed over and supported by the shuttle member 42, and the guidewire 208 is slidably received within the passageway 76 of the shuttle member 42. Advancement of the guide extension catheter assembly 20 can be facilitated by a distal pushing forced applied by the clinician onto the push member 70. In some embodiments, an additional distal pushing force can be applied onto the shaft 50. Regardless, the shuttle member 42 provides mechanical and/or structural support to the tubular member 40 sufficient to facilitate delivery of the tubular member 40 through a tortuous intravascular pathway (e.g., the pathway 206 partially implicated by FIG. 8A).

Figure 8C:
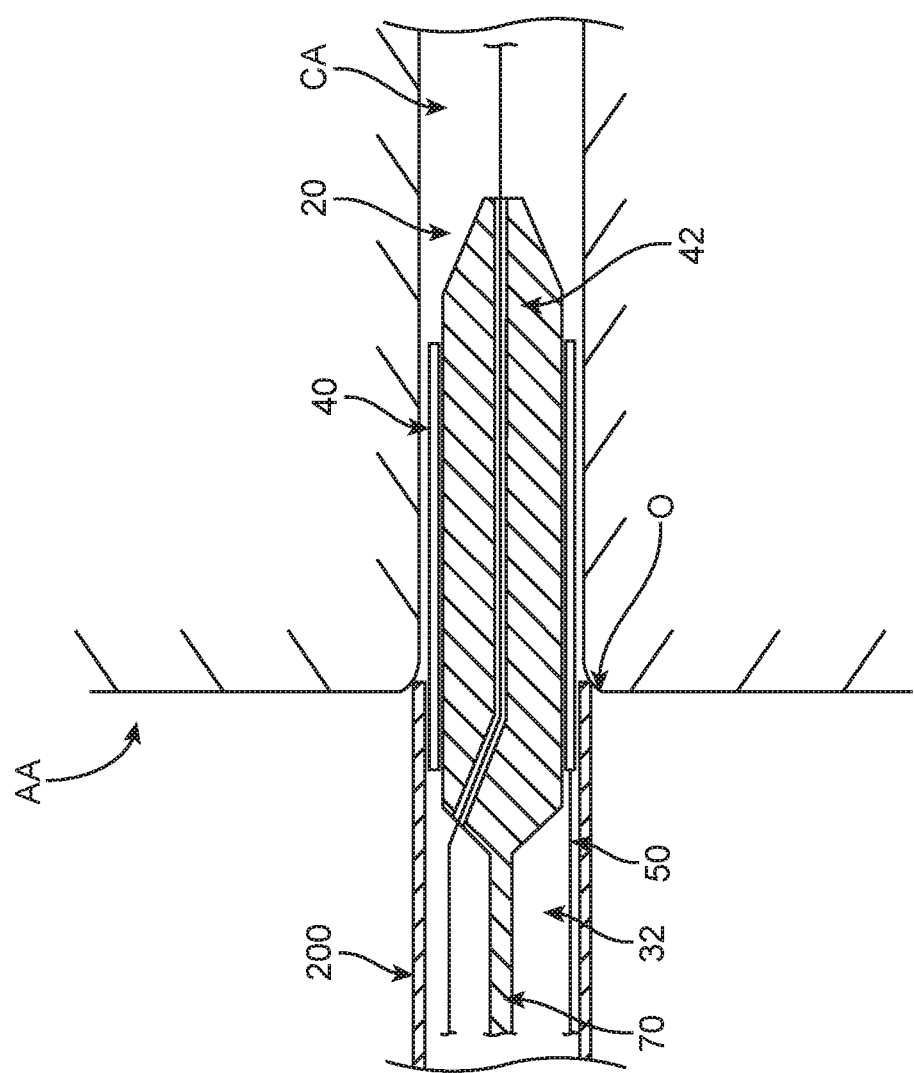

With reference between FIGS. 8A and 8B, distal advancement of the guide extension catheter assembly 20 relative to the guide catheter 200 continues, with the leading end 72 of the shuttle member 42 attaining and then advancing distally beyond the distal side 202 of the guide catheter 200. The tubular member 40 and the shuttle member 42 thus pass through the ostium O and enter the coronary artery CA. The optional tapered tip section 84 of the shuttle member 42 promotes atraumatic contact with tissue/walls of the coronary artery. As reflected by FIG. 8C, distal advancement of the guide extension catheter assembly 20 continues until the tubular member 40 is located at a desired position relative to the guide catheter 200 and the coronary artery CA (e.g., a portion of the tubular member 40 is within the guide catheter 200 and a remainder of the tubular member 40 extends along the coronary artery CA).

Figure 8D:
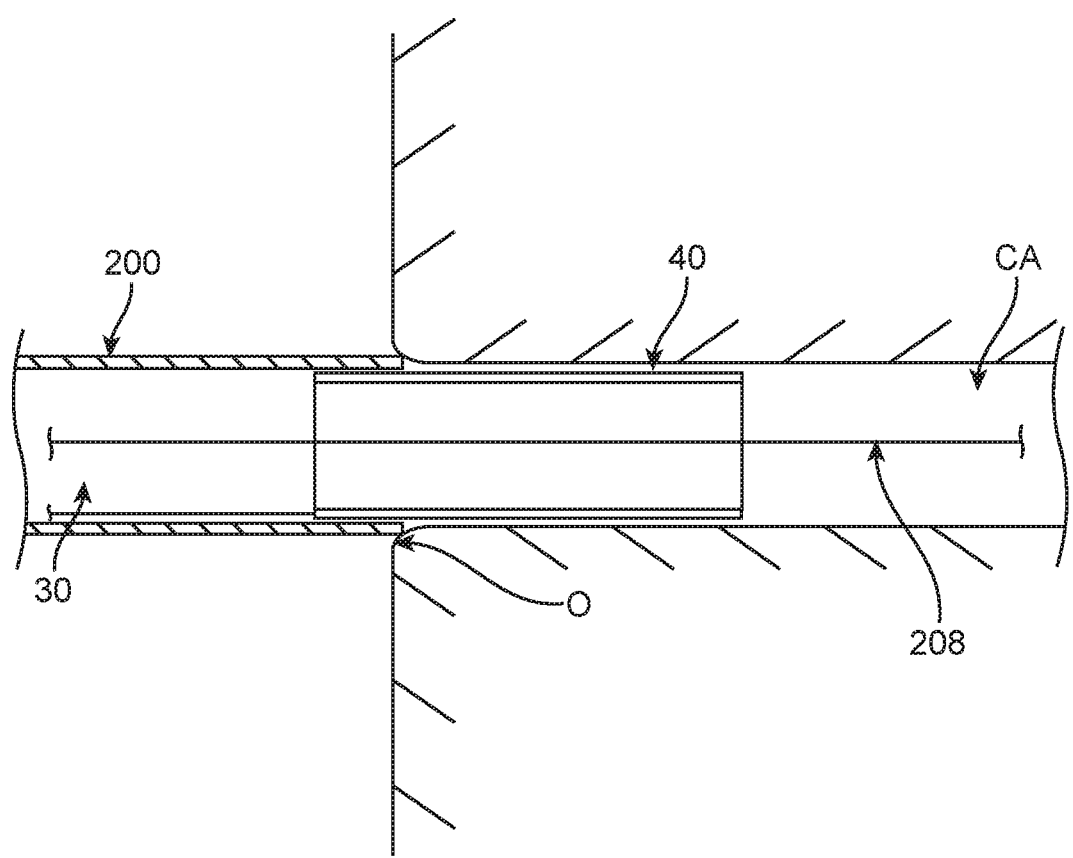

With the tubular member 40 positioned as desired, the support device 32 is removed from the patient. For example, a proximal pulling force is applied by the clinician onto the push member 70 while at the same time a force resisting proximal movement is applied onto the shaft 50. As a result, the shuttle member 42 is caused to retract proximally from the tubular member 40, and the tubular member 40 remains relatively stationary relative to the guide catheter 200 and the coronary artery CA. Complete removal of the support device 32 is reflected by FIG. 8D, illustrating that the guide extension catheter 30, and particular the tubular member 40, has remained at the desired position.

Figure 8E:
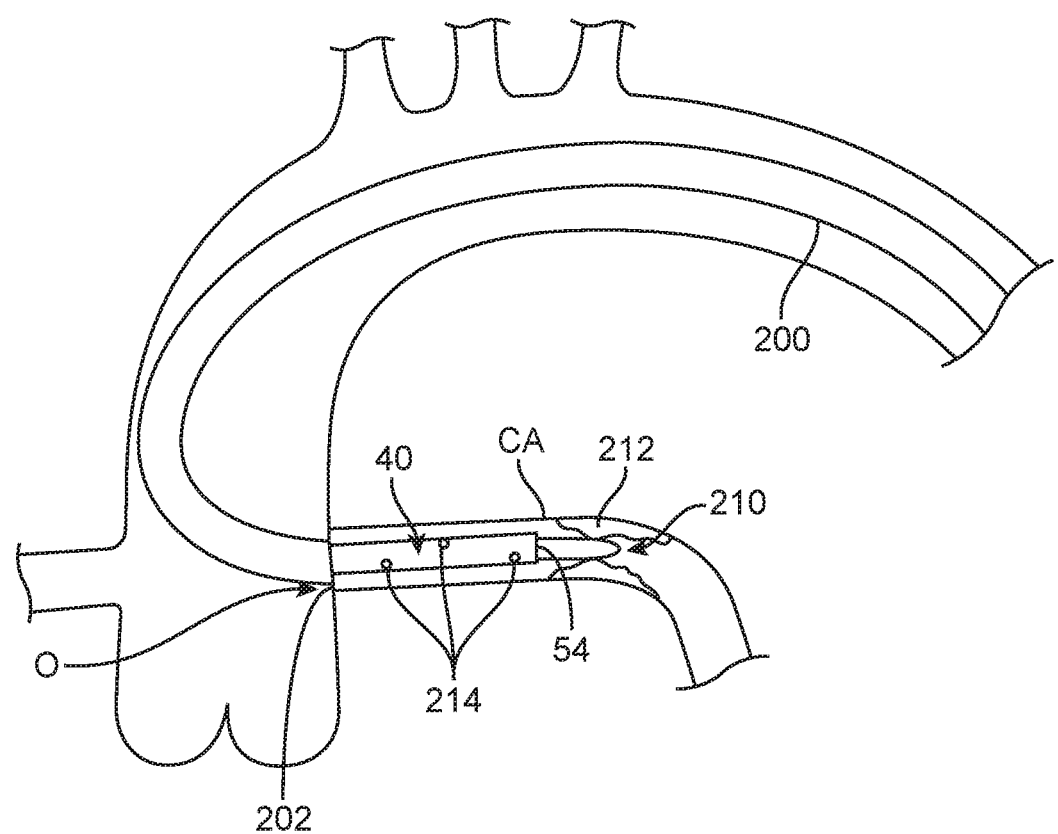

The guide extension catheter 30 is then available to facilitate delivery of an interventional coronary device 210 as generally shown in FIG. 8E. With reference between FIGS. 8D and 8E, the interventional coronary device 210 is delivered through the lumen 204 of the guide catheter 200 and then advanced through the lumen 56 of the tubular member 40. A distal working end of the interventional coronary device 210 (e.g., a stent loaded over a balloon) is advanced distally beyond the distal end 54 of the tubular member 40, and positioned as desired, for example to treat a stenosis 212. FIG. 8E further reflects that in some embodiments, the tubular member 40 can include or define perfusion holes 214.

The guide extension catheter assemblies, coronary treatment systems and methods of the present disclosure provide a marked improvement over previous designs. The shuttle member or delivery shuttle assists in navigating and delivering the guide extension catheter to the target site (e.g., diseased artery). Once in place, the delivery shuttle is removed and the guide extension catheter is left in place to facilitate delivery of additional devices such as a stent. As a purpose of the delivery shuttle is to deliver the guide extension catheter, it can be designed to maximize deliverability of the device, thus sacrificing the mechanical performance of the guide extension catheter if it was a standalone device. However, because the guide extension catheter is not a standalone device, it can be designed with specific or unique features well suited for a particular procedure such as multiple perfusion holes or a thinner wall to give a larger inner diameter/smaller outer diameter.

Although the present disclosure has been described with reference to preferred embodiments, workers skilled in the art will recognize that changes can be made in form and detail without departing from the spirit and scope of the present disclosure.

What is claimed is:

1. A guide extension catheter assembly comprising:
   a guide extension catheter including:
      a shaft,
      a tubular member defining a proximal end opposite a distal end and a lumen open to the proximal and distal ends,
      wherein the shaft is coupled to the tubular member at the proximal end and extends proximally from the proximal end; and
   a support device including:
      a push member,
      a shuttle member defining a leading end opposite a trailing end,
      wherein the push member is coupled to the shuttle member at the trailing end and extends proximally from the trailing end;
   wherein the guide extension catheter assembly is configured to selectively provide a delivery state in which at least a portion of the shuttle member is disposed within the lumen, the leading end is distal the distal end, and the shuttle member is directly, physically connected to the tubular member such that a longitudinal distal force applied to the push member is transferred to the tubular member as a longitudinal distal force via the shuttle member, wherein a maximum outer diameter of an entirety of the shuttle member distal the distal end of the tubular member is not greater than a minimum diameter of the lumen in the delivery state.

2. The guide extension catheter assembly of claim 1, wherein the guide extension catheter assembly is configured to further provide a released state in which the shuttle member is free of direct, physical connection to the tubular member.

3. The guide extension catheter assembly of claim 2, wherein the released state includes the shuttle member moving proximally from the tubular member in response to a longitudinal proximal force applied to the push member.

4. The guide extension catheter assembly of claim 3, further comprising complementary connection features configured to selectively directly, physically connect the tubular member and the shuttle member.

5. The guide extension catheter assembly of claim 4, wherein the shuttle member defines a trailing segment including the trailing end, and further wherein the complementary connection features include a trailing segment of the shuttle member forming a shoulder sized and shaped to abut the proximal end of the tubular member with distal advancement of the shuttle member through the lumen.

6. The guide extension catheter assembly of claim 4, wherein the complementary connection features include a first ramp surface defined at an interior of the tubular member proximate the proximal end and a second ramp surface defined at an exterior of the shuttle member proximate the trailing end, wherein the ramp surfaces are sized and shaped to engage one another with distal advancement of the shuttle member through the lumen.

7. The guide extension catheter assembly of claim 4, wherein the complementary connection features include a slot formed in one of the tubular member and the shuttle member and a post carried by the other of the tubular member and the shuttle member, and further wherein the post is sized and shaped to selectively nest within the slot.

8. The guide extension catheter assembly of claim 1, wherein an outer diameter of the shaft is less than an outer diameter of the tubular member, and an outer diameter of the push member is less than an outer diameter of the shuttle member.

9. The guide extension catheter assembly of claim 1, wherein a maximum outer diameter of the shuttle member along at least a majority of the shuttle member including the leading end is not greater than a minimum diameter of the lumen.

10. The guide extension catheter assembly of claim 1, wherein a hoop strength of the shuttle member is greater than a hoop strength of the tubular member.

11. The guide extension catheter assembly of claim 1, wherein the tubular member defines a plurality of perfusion holes.

12. The guide extension catheter assembly of claim 1, wherein the shuttle member includes a tapering, atraumatic tip at the leading end.

13. The guide extension catheter assembly of claim 1, wherein the shuttle member defines a passageway open to the leading end.

14. A coronary treatment system comprising:
a guide catheter;
a guide extension catheter assembly including:
a guide extension catheter including:
a shaft,
a tubular member defining a proximal end opposite a distal end and a lumen open to the proximal and distal ends,
wherein the shaft is coupled to the tubular member at the proximal end and extends proximally from the proximal end, and
a support device including:
a push member,
a shuttle member defining a leading end opposite a trailing end,
wherein the push member is coupled to the shuttle member at the trailing end and extends proximally from the trailing end,
wherein the guide extension catheter assembly is configured to selectively provide a delivery state in which at least a portion of the shuttle member is disposed within the lumen, the leading end is distal the distal end, and the shuttle member is directly, physically connected to the tubular member such that a longitudinal distal force applied to the push member is transferred to the tubular member as a longitudinal distal force via the shuttle member, wherein a maximum outer diameter of an entirety of the shuttle member distal the distal end of the tubular member is not greater than a minimum diameter of the lumen in the delivery state; and
an interventional coronary device.

15. The coronary treatment system of claim 14, wherein the guide catheter defines a lumen sized and shaped to slidably receive the tubular member and the shuttle member in the delivery state.

16. The coronary treatment system of claim 14, wherein the lumen of the guide catheter is sized to slidably receive a working end of the interventional coronary device.

17. The coronary treatment system of claim 14, further comprising a guidewire.

18. A method of percutaneously accessing an intravascular target region, the method comprising:
positioning a distal side of a guide catheter adjacent to an ostium of a target vessel;
arranging a guide extension catheter assembly to a delivery state, the guide extension catheter assembly including:
a guide extension catheter including:
a shaft,
a tubular member defining a proximal end opposite a distal end and a lumen open to the proximal and distal ends,
wherein the shaft is coupled to the tubular member at the proximal end and extends proximally from the proximal end, and
a support device including:
a push member,
a shuttle member defining a leading end opposite a trailing end,
wherein the push member is coupled to the shuttle member at the trailing end and extends proximally from the trailing end,
wherein the delivery state includes at least a portion of the shuttle member disposed within the lumen, the leading end distal the distal end, and the shuttle member directly, physically connected to the tubular member such that a longitudinal distal force applied to the push member is transferred to the tubular member as a longitudinal distal force via the shuttle member;
advancing the guide extension catheter assembly in the delivery state through the guide catheter such that at least a region of the tubular member projects distally beyond the distal side and the leading end of the shuttle member is distally beyond the distal side, wherein the step of advancing includes the tubular member and the shuttle member moving in tandem;
transitioning the guide extension catheter assembly from the delivery state, including removing the support device from the guide extension catheter; and
advancing an interventional coronary device through the guide catheter and the tubular member.

19. The method of claim 18, wherein the step of positioning includes sliding the guide catheter over a guidewire.

20. The method of claim 18, wherein the tubular member defines a plurality of perfusion holes, and further wherein the step of advancing includes locating the tubular member such that at least some of the perfusion holes are distally beyond the distal side of the guide catheter.

* * * * *